(12) United States Patent
Boualleg et al.

(10) Patent No.: US 11,779,915 B2
(45) Date of Patent: Oct. 10, 2023

(54) PROCESS FOR PREPARING SELECTIVE HYDROGENATION CATALYST, COMPRISING A STEP OF FORMING A NI—CU ALLOY IN PRE-IMPREGNATION

(71) Applicant: IFP Energies nouvelles, Rueil-Malmaison (FR)

(72) Inventors: Malika Boualleg, Rueil-Malmaison (FR); Anne-Agathe Quoineaud, Rueil-Malmaison (FR)

(73) Assignee: IFP Energies nouvelles, Rueil-Malmaison (FR)

( * ) Notice: Subject to any disclaimer, the term of this patent is extended or adjusted under 35 U.S.C. 154(b) by 197 days.

(21) Appl. No.: 17/423,039

(22) PCT Filed: Jan. 8, 2020

(86) PCT No.: PCT/EP2020/050329
§ 371 (c)(1),
(2) Date: Jul. 14, 2021

(87) PCT Pub. No.: WO2020/148131
PCT Pub. Date: Jul. 23, 2020

(65) Prior Publication Data
US 2022/0062886 A1 Mar. 3, 2022

(30) Foreign Application Priority Data

Jan. 15, 2019 (FR) ...................................... 1900335

(51) Int. Cl.
| | | |
|---|---|---|
| *B01J 37/18* | (2006.01) | |
| *B01J 23/755* | (2006.01) | |
| *B01J 37/08* | (2006.01) | |
| *B01J 37/20* | (2006.01) | |
| *C07C 5/03* | (2006.01) | |
| *C07C 5/10* | (2006.01) | |

(52) U.S. Cl.
CPC ............ *B01J 37/18* (2013.01); *B01J 23/755* (2013.01); *B01J 37/08* (2013.01); *B01J 37/20* (2013.01); *C07C 5/03* (2013.01); *C07C 5/10* (2013.01)

(58) Field of Classification Search
CPC . B01J 37/18; B01J 23/755; B01J 37/08; B01J 37/20; C07C 5/03; C07C 5/10
USPC ........................... 502/337; 585/250, 259, 440
See application file for complete search history.

(56) References Cited

U.S. PATENT DOCUMENTS

| | | |
|---|---|---|
| 5,948,942 A | 9/1999 | Ramirez De Agudelo et al. |
| 9,695,095 B2 * | 7/2017 | Dubreuil .................. B01J 37/16 |
| 2003/0191020 A1 | 10/2003 | Bharadwaj et al. |
| 2005/0209491 A1 | 9/2005 | Ryu et al. |
| 2006/0084830 A1 | 4/2006 | Ryu et al. |
| 2017/0259249 A1 | 9/2017 | Boualleg et al. |
| 2018/0154340 A1 * | 6/2018 | Boualleg ................ B01J 23/892 |

FOREIGN PATENT DOCUMENTS

| | | |
|---|---|---|
| EP | 1114013 B1 | 11/2002 |
| WO | 2016037830 A1 | 3/2016 |

OTHER PUBLICATIONS

International Search Report for PCT/EP2020/050329 dated Mar. 10, 2020.
Nataj, Seyedeh Molood Masoom et al., "Modeling and optimization of methane dry reforming over Ni—Cu/Al2O3 Catalyst using Box-Behnken design," Journal of Energy Chemistry, 2018, vol. 27, pp. 1475-1488.
Obregón, Iker et al., "Structure-activity relation of Ni—Cu/Al2O3 catalyst for gamma-valerolactone conversion to 2-methyltetrahydrofuran," Applied Catalysis B: Environmental, 2017, vol. 210, pp. 328-341.

* cited by examiner

*Primary Examiner* — Patricia L. Hailey
(74) *Attorney, Agent, or Firm* — MILLEN WHITE ZELANO & BRANIGAN, PC; Brion P. Heaney

(57) ABSTRACT

A process for preparing a selective hydrogenation catalyst comprising nickel, copper and a support comprising at least one refractory oxide, comprising the following steps:
bringing the support into contact with a solution containing at least one copper precursor and one nickel precursor;
drying the catalyst precursor at a temperature of less than 250° C.;
reducing the catalyst precursor by bringing said precursor into contact with a reducing gas at a temperature of between 150° C. and 250° C.;
bringing the catalyst precursor into contact with a solution comprising a nickel precursor;
a step of drying the catalyst precursor at a temperature of less than 250° C.;
reducing the catalyst precursor by bringing said precursor into contact with a reducing gas at a temperature of between 150° C. and 250° C.

19 Claims, No Drawings

PROCESS FOR PREPARING SELECTIVE HYDROGENATION CATALYST, COMPRISING A STEP OF FORMING A NI—CU ALLOY IN PRE-IMPREGNATION

TECHNICAL FIELD

The present invention relates to a process for preparing a supported metallic catalyst, comprising nickel and copper, intended particularly for the hydrogenation of unsaturated hydrocarbons.

The present invention also relates to the use of these catalysts in reactions for the hydrogenation of unsaturated hydrocarbons, and more particularly selective hydrogenation of olefinic fractions.

STATE OF THE ART

Catalysts for the selective hydrogenation of polyunsaturated compounds are generally based on metals from Group VIII of the Periodic Table of the Elements, such as nickel. The metal is in the form of nanometric metal particles deposited on a support which may be a refractory oxide. The content of group VIII metal, the optional presence of a second metal element, the size of the metal particles and the distribution of the active phase in the support and also the nature and the pore distribution of the support are parameters which may have an influence on the performance of the catalysts.

The rate of the hydrogenation reaction is governed by several criteria, such as the diffusion of the reactants toward the surface of the catalyst (external diffusional limitations), the diffusion of the reactants in the porosity of the support toward the active sites (internal diffusional limitations) and the intrinsic properties of the active phase, such as the size of the metallic particles and the distribution of the active phase within the support.

The promotion of a nickel-based catalyst has frequently been proposed in order to improve performance levels in selective hydrogenation. For example, it is known from U.S. Pat. No. 5,208,405 to use a catalyst based on nickel and silver for the selective hydrogenation of $C_4$-$C_{10}$ diolefins.

Furthermore, it is known to promote nickel, predominantly present, with metals of group IB, in particular gold (FR 2 949 077) or tin (FR 2 949 078). Document FR 3 011 844 discloses a catalyst for the implementation of a selective hydrogenation process comprising a support and an active metallic phase deposited on the support, the active metallic phase comprising copper and at least one nickel or cobalt metal in a Cu:(Ni and/or Co) mole ratio greater than 1.

Moreover, prior to the employment of such catalysts and the use thereof in a hydrogenation process, a step of reducing treatment in the presence of a reducing gas is carried out so as to obtain a catalyst comprising an active phase at least partially in metallic form. This treatment makes it possible to activate the catalyst and to form metallic particles. This treatment may be carried out in situ or ex situ, that is to say after or before the catalyst is charged to the hydrogenation reactor.

SUBJECTS OF THE INVENTION

Continuing its research in the field of hydrogenating catalysts, the applicant has now surprisingly discovered that it is possible to prepare catalysts which are particularly active in the selective hydrogenation of polyunsaturated hydrocarbon fractions after reduction at low temperature, by carrying out a specific preparation process wherein an alloy based on nickel and copper is formed on the support before depositing on the support the precursor of the active phase (based on nickel) of the catalyst.

Without wishing to be bound by any theory, it has been observed by the applicant that, during the preparation of the catalyst, carrying out a step of bringing the support into contact with a solution simultaneously containing a copper-based metal precursor and a nickel-based metal precursor, followed by a step of drying and reducing in the presence of a reducing gas at low temperature (between 150° C. and 250° C.) makes it possible to obtain a nickel-copper alloy (in reduced form) which unexpectedly makes it possible to greatly improve the reducibility of the nickel active phase on the support, said nickel active phase being supplied for the most part in a step subsequent to the formation of the nickel-copper alloy (in reduced form). The preparation process according to the invention thus makes it possible to carry out a step of reducing the metal elements in the presence of a reducing gas at lower temperatures and shorter reaction times than those commonly used in the prior art. Advantageously, the use of less severe operating conditions than in the prior art makes it possible to directly carry out the reduction step within the reactor in which it is desired to carry out the selective hydrogenation of polyunsaturated fractions. Furthermore, the presence of copper in the catalyst makes it possible to maintain good activity and a longer service life of the catalyst when the latter is placed in contact with a hydrocarbon feedstock comprising sulfur, notably steam cracking and/or catalytic cracking C3 hydrocarbon fractions. Indeed, compared to nickel, the copper present in the catalyst more easily captures the sulfur-containing compounds included in the feedstock, thereby avoiding irreversibly poisoning the most virulent active sites of the nickel which exist on the new catalyst.

A subject of the present invention is a process for preparing a catalyst for the selective hydrogenation of polyunsaturated hydrocarbon fractions comprising a metallic active phase based on nickel, in a proportion of 1% to 35% by weight of nickel element relative to the total weight of the catalyst, and based on copper, in a proportion of 0.5% to 15% by weight of copper element relative to the total weight of the catalyst, and a support comprising at least one refractory oxide chosen from silica, alumina and silica-alumina, said process comprising the following steps:

a) a step of bringing the support into contact with at least one solution containing at least one copper precursor and one nickel precursor at a desired nickel concentration is carried out in order to obtain, on the final catalyst, a content of between 0.5% and 15% by weight of nickel element relative to the total weight of the final catalyst;

b) at least one step of drying the catalyst precursor resulting from step a) is carried out at a temperature of less than 250° C.;

c) optionally, a heat treatment of the catalyst precursor obtained at the end of step b) is carried out at a temperature of between 250 and 1000° C., in the presence or absence of water;

d) the catalyst precursor resulting from step b), optionally step c), is reduced by bringing said catalyst precursor into contact with a reducing gas at a temperature of between 150 and 250° C.;

e) a step of bringing the catalyst precursor obtained at the end of step d) into contact with a solution comprising at least one nickel precursor is carried out;

f) at least one step of drying the catalyst precursor resulting from step e) is carried out at a temperature of less than 250° C.;

g) optionally, a heat treatment of the catalyst precursor obtained at the end of step f) is carried out at a temperature of between 250 and 1000° C., in the presence or absence of water;

h) the catalyst precursor resulting from step f), optionally step g), is reduced by bringing said catalyst precursor into contact with a reducing gas at a temperature of between 150 and 250° C.

Advantageously, in step a) the mole ratio between nickel and copper is between 0.5 and 5.

Preferably, step d) and/or h) is (are) carried out at a temperature of between 160 and 230° C.

More preferentially, step d) and/or h) is (are) carried out at a temperature of between 170 and 220° C.

Advantageously, steps d) and/or h) is (are) carried out for between 10 minutes and 110 minutes.

Advantageously, the preparation process also comprises a step of passivation of the catalyst precursor with a sulfur-containing compound after the reduction step d) but before step e), and/or after the reduction step h).

Preferably, the passivation step(s) is (are) carried out at a temperature of between 20 and 350° C. for 10 to 240 minutes.

Advantageously, said sulfur-containing compound is chosen from thiophene, thiophane, dimethyl sulfide, diethyl sulfide, dipropyl sulfide, propylmethyl sulfide, dithiodiethanol.

Advantageously, the copper precursor is chosen from copper acetate, copper acetylacetonate, copper nitrate, copper sulfate, copper chloride, copper bromide, copper iodide or copper fluoride.

Advantageously, the copper precursor is copper nitrate.

Advantageously, the reducing gas of step d) and/or h) is dihydrogen.

Advantageously, the hydrogen flow rate, expressed in l/hour/gram of catalyst precursor, is between 0.01 and 100 l/hour/gram of catalyst precursor.

Advantageously, the nickel precursor supplied during step a) and/or e) is chosen from nickel nitrate, nickel carbonate or nickel hydroxide.

Another subject according to the invention relates to a process for the selective hydrogenation of polyunsaturated compounds containing at least 2 carbon atoms per molecule, such as diolefins and/or acetylenics and/or alkenylaromatics, present in a hydrocarbon feedstock having a final boiling point of less than or equal to 300° C., said process being carried out at a temperature of between 0 and 300° C., at a pressure of between 0.1 and 10 MPa, at a hydrogen/(polyunsaturated compounds to be hydrogenated) mole ratio of between 0.1 and 10 and at an hourly space velocity of between 0.1 and 200 $h^{-1}$ when the process is carried out in the liquid phase, or at a hydrogen/(polyunsaturated compounds to be hydrogenated) mole ratio of between 0.5 and 1000 and at an hourly space velocity of between 100 and 40 000 $h^{-1}$ when the process is carried out in the gas phase, in the presence of a catalyst obtained according to the preparation process according to the invention.

DETAILED DESCRIPTION OF THE INVENTION

1. Definitions

Subsequently, the groups of chemical elements are given according to the CAS classification (CRC Handbook of Chemistry and Physics, published by CRC Press, editor-in-chief D. R. Lide, 81st edition, 2000-2001). For example, group VIII according to the CAS classification corresponds to the metals of columns 8, 9 and 10 according to the new IUPAC classification.

The degree of reduction (DR) of a metal M contained in the catalyst is defined as being the percentage of said metal M reduced after the step of reducing said catalyst. The degree of reduction (DR) corresponds to the ratio between the amount of metal reduced (M1) and the amount of theoretically reducible metal present on the catalyst, measured by X-ray fluorescence (M2), i.e. DR (%)=(M1/M2)× 100. In the context of the present invention, the degree of reduction of the nickel (Ni) was measured by X-ray diffraction (XRD) analysis. The description of the method for measuring the amount of reducible metal on oxide catalysts is explained later in the description (cf. examples section).

The expression "the specific surface of the catalyst or of the support used for the preparation of the catalyst according to the invention" is intended to mean the BET specific surface determined by nitrogen adsorption in accordance with standard ASTM D 3663-78 drawn up from the Brunauer-Emmett-Teller method described in the journal "The Journal of the American Chemical Society", 60, 309 (1938).

In the present application, the term "to comprise" is synonymous with (means the same thing as) "to include" and "to contain", and is inclusive or open and does not exclude other elements not stated. It is understood that the term "to comprise" includes the exclusive and closed term "to consist of".

The term "macropores" is intended to mean pores, the opening of which is greater than 50 nm.

The term "mesopores" is intended to mean pores, the opening of which is between 2 nm and 50 nm, limits included.

The term "micropores" is intended to mean pores, the opening of which is less than 2 nm.

The term "total pore volume" of the catalyst or of the support used for the preparation of the catalyst according to the invention is intended to mean the volume measured by intrusion with a mercury porosimeter according to standard ASTM D4284-83 at a maximum pressure of 4000 bar (400 MPa), using a surface tension of 484 dyne/cm and a contact angle of 140°. The wetting angle was taken equal to 140° following the recommendations of the work "Techniques de l'énieur, traité analyse et caractérisation" [Techniques of the Engineer, Analysis and Characterization Treatise], pages 1050-1055, written by Jean Charpin and Bernard Rasneur.

In order to obtain better accuracy, the value of the total pore volume corresponds to the value of the total pore volume measured by intrusion with a mercury porosimeter measured on the sample minus the value of the total pore volume measured by intrusion with a mercury porosimeter measured on the same sample for a pressure corresponding to 30 psi (approximately 0.2 MPa).

The volume of the macropores and of the mesopores is measured by porosimetry by intrusion of mercury according to standard ASTM D4284-83 at a maximum pressure of 4000 bar (400 MPa), using a surface tension of 484 dyne/cm and a contact angle of 140°. The value from which the mercury fills all the intergranular voids is set at 0.2 MPa and it is considered that, above this, the mercury penetrates into the pores of the sample.

The macropore volume of the catalyst or of the support used for the preparation of the catalyst according to the invention is defined as being the cumulative volume of mercury introduced at a pressure of between 0.2 MPa and 30 MPa, corresponding to the volume present in the pores with an apparent diameter of greater than 50 nm.

The mesopore volume of the catalyst or of the support used for the preparation of the catalyst according to the invention is defined as being the cumulative volume of mercury introduced at a pressure of between 30 MPa and 400 MPa, corresponding to the volume present in the pores with an apparent diameter of between 2 and 50 nm.

The micropore volume is measured by nitrogen porosimetry. The quantitative analysis of the microporosity is performed using the "t" method (method of Lippens-De Boer, 1965), which corresponds to a transform of the starting adsorption isotherm, as described in the work "Adsorption by powders and porous solids. Principles, methodology and applications", written by F. Rouquérol, J. Rouquérol and K. Sing, Academic Press, 1999.

The median mesopore diameter is also defined as being the diameter such that, out of the combined pores constituting the mesopore volume, all the pores with a size of less than this diameter constitute 50% of the total mesopore volume determined by intrusion with a mercury porosimeter.

The median macropore diameter is also defined as being the diameter such that, out of the combined pores constituting the macropore volume, all the pores with a size of less than this diameter constitute 50% of the total macropore volume determined by intrusion with a mercury porosimeter.

2. Detailed Description

Process for Preparing the Catalyst

According to the invention, the process for preparing a catalyst for the selective hydrogenation of polyunsaturated hydrocarbon fractions comprising, preferably consisting of, a metallic active phase based on nickel, in a proportion of 1% to 35% by weight of nickel element relative to the total weight of the catalyst, and based on copper, in a proportion of 0.5% to 15% by weight of copper element relative to the total weight of the catalyst, and a support comprising at least one refractory oxide chosen from silica, alumina and silica-alumina, comprises, preferably consists of, the following steps:

a) a step of bringing the support into contact with at least one solution containing at least, preferably consisting of, one copper precursor and one nickel precursor at a desired nickel concentration is carried out in order to obtain, on the final catalyst, a content of between 0.5% and 15% by weight of nickel element relative to the total weight of the final catalyst;

b) at least one step of drying the catalyst precursor resulting from step a) is carried out at a temperature of less than 250° C.;

c) optionally, a heat treatment of the catalyst precursor obtained at the end of step b) is carried out at a temperature of between 250 and 1000° C., in the presence or absence of water;

d) the catalyst precursor resulting from step b), optionally step c), is reduced by bringing said catalyst precursor into contact with a reducing gas at a temperature of between 150 and 250° C.;

e) a step of bringing the catalyst precursor obtained at the end of step d) into contact with a solution comprising at least, preferably consisting of, one nickel precursor is carried out;

f) at least one step of drying the catalyst precursor resulting from step e) is carried out at a temperature of less than 250° C.;

g) optionally, a heat treatment of the catalyst precursor obtained at the end of step f) is carried out at a temperature of between 250 and 1000° C., in the presence or absence of water;

h) the catalyst precursor resulting from step f), optionally step g), is reduced by bringing said catalyst precursor into contact with a reducing gas at a temperature of between 150 and 250° C.;

i) optionally, a step i) of passivation with a sulfur-containing compound is carried out after the reducing treatment step h).

Steps a) to i) of said preparation process are described in detail below.

Step a) Bringing a Nickel Precursor and a Copper Precursor into Contact with the Support The deposition of nickel and copper on said support, in accordance with the implementation of step a), can be carried out by dry impregnation or excess impregnation, or also by deposition—precipitation, according to methods well known to those skilled in the art.

Said step a) is preferentially carried out by impregnation of the support consisting for example in bringing said support into contact with at least one solution, aqueous or organic (for example methanol or ethanol or phenol or acetone or toluene or dimethyl sulfoxide (DMSO)) or else consisting of a mixture of water and at least one organic solvent, comprising, preferably consisting of, at least one nickel precursor and at least one copper precursor at least partially in the dissolved state, or else in bringing said support into contact with at least one colloidal solution comprising, preferably consisting of, at least one nickel precursor and one copper precursor in oxidized form (nanoparticles of oxide, of oxy(hydroxide) or of hydroxide of nickel and copper) or in reduced form (metallic nanoparticles of nickel and copper in the reduced state). Preferably, the solution is aqueous. The pH of this solution may be modified by the optional addition of an acid or of a base.

Preferably, said step a) is carried out by dry impregnation, which consists in bringing the catalyst support into contact with a solution comprising, preferably consisting of, at least one nickel precursor and at least one copper precursor, the volume of the solution of which is between 0.25 and 1.5 times the pore volume of the support to be impregnated.

When the nickel precursor is introduced in aqueous solution, a nickel precursor is advantageously used in the form of nitrate, carbonate, acetate, chloride, hydroxide, hydroxycarbonate, oxalate, sulfate or formate, of complexes formed by a polyacid or an acid-alcohol and its salts, of complexes formed with acetylacetonates, of tetrammine or hexammine complexes, or else of any other inorganic derivative soluble in aqueous solution, which is placed in contact with said support. Preferably, nickel nitrate, nickel hydroxide, nickel carbonate, nickel chloride or nickel hydroxycarbonate is advantageously used as nickel precursor. Very preferably, the nickel precursor is nickel nitrate, nickel carbonate or nickel hydroxide.

When the copper precursor is introduced in aqueous solution, a copper precursor in mineral or organic form is advantageously used. In mineral form, the copper precursor can be chosen from copper acetate, copper acetylacetonate, copper nitrate, copper sulfate, copper chloride, copper bromide, copper iodide or copper fluoride. Very preferably, the copper precursor salt is copper nitrate.

According to the invention, the nickel precursor is supplied in step a) at a desired concentration in order to obtain on the final catalyst (i.e. obtained at the end of the reduction step h) or the passivation step i) if the latter is carried out)

a content of between 0.5% and 15% by weight of nickel element relative to the total weight of the final catalyst, preferably between 0.5% and 10% by weight, more preferentially between 1% and 8% by weight, even more preferentially between 1% and 5% by weight.

The amounts of the copper precursor(s) introduced into the solution according to step a) are chosen such that the total copper content is between 0.5% and 15% by weight of copper element relative to the total weight of the final catalyst (i.e. obtained at the end of the reduction step h) or the passivation step i) if the latter is carried out), preferably between 0.5% and 12% by weight, preferably between 0.75% and 10% by weight, and even more preferentially between 1% and 9% by weight.

Step b) Drying the Impregnated Support

Step b) of drying the impregnated support is carried out at a temperature of less than 250° C., preferably of between 15 and 180° C., more preferentially between 30 and 160° C., even more preferentially between 50 and 150° C., and even more preferentially between 70 and 140° C., for a period typically of between 10 minutes and 24 hours. Longer periods of time are not ruled out, but do not necessarily afford any improvement.

The drying step can be carried out by any technique known to those skilled in the art. It is advantageously carried out under an inert atmosphere or under an oxygen-containing atmosphere or under a mixture of inert gas and oxygen. It is advantageously carried out at atmospheric pressure or at reduced pressure. Preferably, this step is carried out at atmospheric pressure and in the presence of air or of nitrogen.

Step c) Heat Treatment of the Dried Catalyst (Optional Step)

The catalyst precursor obtained at the end of step b) can undergo an additional heat treatment step, before the reduction step d), at a temperature of between 250 and 1000° C. and preferably between 250 and 750° C., for a period typically between 15 minutes and 10 hours, under an inert atmosphere or under an oxygen-containing atmosphere, optionally in the presence of water. Longer treatment times are not ruled out, but do not necessarily afford an improvement.

The term "heat treatment" is intended to mean temperature treatment respectively without the presence or in the presence of water. In the latter case, contact with the steam can take place at atmospheric pressure or under autogenous pressure. Several combined cycles without the presence or with the presence of water can be performed.

In the event of water being present, the water content is preferably between 150 and 900 grams per kilogram of dry air and even more preferably between 250 and 650 grams per kilogram of dry air.

Thus, after the drying step b), or after the optional heat treatment step c), the catalyst precursor comprises nickel in oxide form, that is to say in NiO form, and copper in oxide form, that is to say in CuO form.

Step d) Reduction with a Reducing Gas

According to the invention, a step of reducing treatment d) of the dried catalyst obtained at the end of step b) or of the catalyst obtained at the end of step c) is carried out in the presence of a reducing gas so as to form on the catalyst support a nickel-copper alloy at least partially in metallic form. The reducing gas is preferably hydrogen. The hydrogen can be used pure or as a mixture (for example a hydrogen/nitrogen, hydrogen/argon or hydrogen/methane mixture). In the case where the hydrogen is used as a mixture, all proportions can be envisaged.

According to one essential aspect of the preparation process according to the invention, said reducing treatment is carried out at a temperature of between 150° C. and 250° C., preferably of between 160 and 230° C., and more preferentially between 170 and 220° C. The duration of the reducing treatment is between 5 minutes and less than 5 hours, preferably between 10 minutes and 4 hours, and even more preferentially between 10 minutes and 110 minutes.

It has been observed by the applicant that step d) of reduction with a reducing gas makes it possible to form a nickel-copper alloy at least partially in metallic form. The nickel-copper alloy satisfies the formula $Ni_xCu_y$, with x between 0.1 and 0.9 and y between 0.1 and 0.9.

The rise in temperature up to the desired reduction temperature is generally slow, for example set between 0.1 and 10° C./min, preferably between 0.3 and 7° C./min.

The hydrogen flow rate, expressed in l/hour/gram of catalyst precursor, is between 0.01 and 100 l/hour/gram of catalyst, preferably between 0.05 and 10 l/hour/gram of catalyst precursor and more preferably still between 0.1 and 5 l/hour/gram of catalyst precursor.

Passivation (Optional Step)

The catalyst precursor obtained at the end of the reduction step d) can advantageously be passivated before carrying out the step of bringing said catalyst precursor into contact with a solution comprising, preferably consisting of, at least one nickel precursor (step e).

When carried out, the step of passivation of the catalyst precursor obtained at the end of step d) is carried out with a sulfur-containing compound which makes it possible to improve the selectivity of the catalysts and to avoid thermal runaway during the start-up of new catalysts.

The passivation generally consists in irreversibly poisoning, by the sulfur-containing compound, the most virulent active sites of the nickel which exist on the new catalyst and thus in weakening the activity of the catalyst in favor of its selectivity. The passivation step is carried out by the use of methods known to those skilled in the art.

The passivation step with a sulfur-containing compound is generally carried out at a temperature of between 20 and 350° C., preferably between 40 and 200° C., for 10 to 240 minutes. The sulfur-containing compound is, for example, chosen from the following compounds: thiophene, thiophane, alkyl monosulfides, such as dimethyl sulfide, diethyl sulfide, dipropyl sulfide and propyl methyl sulfide, or also an organic disulfide of formula HO—$R_1$—S—S—$R_2$—OH, such as dithiodiethanol of formula HO—$C_2H_4$—S—S—$C_2H_4$—OH (often referred to as DEODS). The sulfur content is generally between 0.1% and 2% by weight of said element relative to the total weight of the catalyst.

Step e) Bringing the Catalyst Precursor into Contact with a Solution Comprising a Nickel Precursor The deposition of nickel, in accordance with the implementation of step e), can be carried out by dry impregnation or excess impregnation, or else by deposition—precipitation, according to methods well known to those skilled in the art.

Said step e) is preferentially carried out by impregnating the catalyst precursor obtained at the end of step d) (or after the optional passivation step) consisting for example in bringing the catalyst precursor into contact with at least one solution, aqueous or organic (for example methanol or ethanol or phenol or acetone or toluene or dimethyl sulfoxide (DMSO)), or else consisting of a mixture of water and at least one organic solvent, comprising, preferably consisting of, at least one nickel precursor at least partially in the dissolved state, or else in bringing the catalyst precursor into contact with at least one colloidal solution comprising, preferably consisting of, at least one nickel precursor, in oxidized form (nanoparticles of oxides, oxy(hydroxide) or hydroxide of nickel) or in reduced form (metallic nanoparticles of nickel in the reduced state). Preferably, the solution is aqueous. The pH of this solution will be able to be modified by the optional addition of an acid or of a base.

Preferably, said step e) is carried out by dry impregnation, which consists in bringing the catalyst precursor into contact with at least one solution containing, preferably consisting of, at least one nickel precursor, the volume of the solution of which is between 0.25 and 1.5 times the pore volume of the support of the catalyst precursor to be impregnated.

When the nickel precursor is introduced in aqueous solution, use is advantageously made of a nickel precursor in the nitrate, carbonate, chloride, sulfate, hydroxide, hydroxycarbonate, formate, acetate or oxalate form, in the form of complexes formed with acetylacetonates, or also in the form of tetrammine or hexammine complexes, or in the form of any other inorganic derivative which is soluble in aqueous solution, which is brought into contact with said catalyst precursor. Use is advantageously made, as nickel precursor, of nickel nitrate, nickel carbonate, nickel chloride, nickel hydroxide or nickel hydroxycarbonate. Very preferably, the nickel precursor is nickel nitrate, nickel carbonate or nickel hydroxide.

The nickel precursor is supplied in step e) at a desired concentration in order to obtain on the final catalyst (i.e. obtained at the end of the reduction step h) or the passivation step i) if the latter is carried out) a content of between 0.5% and 34.5% by weight of nickel element relative to the total weight of the catalyst.

Step f) Drying the Impregnated Support

Step f) of drying the impregnated support is carried out at a temperature of less than 250° C., preferably of between 15 and 180° C., more preferentially between 30 and 160° C., even more preferentially between 50 and 150° C., and even more preferentially between 70 and 140° C., for a period typically between 10 minutes and 24 hours. Longer periods of time are not ruled out, but do not necessarily afford any improvement.

The drying step can be carried out by any technique known to those skilled in the art. It is advantageously carried out under an inert atmosphere or under an oxygen-containing atmosphere or under a mixture of inert gas and oxygen. It is advantageously carried out at atmospheric pressure or at reduced pressure. Preferably, this step is carried out at atmospheric pressure and in the presence of air or of nitrogen.

g) Heat Treatment of the Dried Catalyst (Optional Step)

The dried catalyst precursor can undergo an additional heat treatment step, before the reduction step h), at a temperature of between 250 and 1000° C. and preferably between 250 and 750° C., for a period typically between 15 minutes and 10 hours, under an inert atmosphere or under an oxygen-containing atmosphere, optionally in the presence of water. Longer treatment times are not ruled out, but do not necessarily afford an improvement.

The term "heat treatment" is intended to mean temperature treatment respectively without the presence or in the presence of water. In the latter case, contact with the steam can take place at atmospheric pressure or under autogenous pressure. Several combined cycles without the presence or with the presence of water can be performed. After this or these treatment(s), the catalyst precursor comprises nickel in the oxide form, that is to say in the NiO form.

In the event of water being present, the water content is preferably between 150 and 900 grams per kilogram of dry air and even more preferably between 250 and 650 grams per kilogram of dry air.

Step h) Reduction with a Reducing Gas

Prior to the use of the catalyst in the catalytic reactor and the implementation of a hydrogenation process, a reducing treatment step h) is carried out in the presence of a reducing gas so as to obtain a catalyst comprising nickel at least partially in the metallic form. This step is advantageously carried out in situ, that is to say after charging of the catalyst to a reactor for selective hydrogenation of polyunsaturated compounds. This treatment makes it possible to activate said catalyst and to form metal particles, in particular of nickel in the zero-valent state. The in-situ implementation of the catalyst reducing treatment makes it possible to dispense with an additional step of passivation of the catalyst with an oxygen-bearing compound or $CO_2$, which is necessarily the case when the catalyst is prepared by carrying out a reducing treatment ex situ, that is to say outside the reactor used for selective hydrogenation.

In fact, when the reducing treatment is carried out ex-situ, it is necessary to carry out a passivation step in order to preserve the metallic phase of the catalyst in the presence of air (during operations of transport and charging of the catalyst to the hydrogenation reactor), then to carry out a new step of reducing the catalyst.

The reducing gas is preferably hydrogen. The hydrogen can be used pure or as a mixture (for example a hydrogen/nitrogen, hydrogen/argon or hydrogen/methane mixture). In the case where the hydrogen is used as a mixture, all proportions can be envisaged.

According to one essential aspect of the preparation process according to the invention, said reducing treatment is carried out at a temperature of between 150° C. and 250° C., preferably of between 160 and 230° C., and more preferentially between 170 and 220° C. The duration of the reducing treatment is between 5 minutes and less than 5 hours, preferably between 10 minutes and 4 hours, and even more preferentially between 10 minutes and 110 minutes.

The presence of the nickel-copper alloy at least partially in reduced form makes it possible to use operating conditions for reducing the nickel active phase which are less severe than in the prior art and thus makes it possible to carry out the reduction step directly within the reactor in which it is desired to carry out the selective hydrogenation of polyunsaturated fractions.

Furthermore, the presence of copper in the catalyst makes it possible to preserve good activity of the catalyst and a good service life of the catalyst when the latter is placed in contact with a hydrocarbon feedstock comprising sulfur, notably steam cracking and/or catalytic cracking C3 hydrocarbon fractions. Indeed, compared to nickel, the copper present in the catalyst more easily captures the sulfur-containing compounds included in the feedstock, thereby avoiding irreversibly poisoning the most virulent active sites of the nickel which exist on the new catalyst.

The rise in temperature up to the desired reduction temperature is generally slow, for example set between 0.1 and 10° C./min, preferably between 0.3 and 7° C./min.

The hydrogen flow rate, expressed in l/hour/gram of catalyst precursor, is between 0.01 and 100 l/hour/gram of catalyst, preferably between 0.05 and 10 l/hour/gram of catalyst precursor and more preferably still between 0.1 and 5 l/hour/gram of catalyst precursor.

Step i) Passivation (Optional)

The catalyst prepared according to the process according to the invention can advantageously undergo a passivation step with a sulfur-containing compound which makes it possible to improve the selectivity of the catalysts and to avoid thermal runaway during the start-up of new catalysts. The passivation generally consists in irreversibly poisoning, by the sulfur-containing compound, the most virulent active sites of the nickel which exist on the new catalyst and thus in weakening the activity of the catalyst in favor of its selectivity. The passivation step is carried out using methods known to those skilled in the art.

The passivation step with a sulfur-containing compound is generally carried out at a temperature of between 20 and 350° C., preferably between 40 and 200° C., for 10 to 240 minutes. The sulfur-containing compound is, for example, chosen from the following compounds: thiophene, thiophane, alkyl monosulfides, such as dimethyl sulfide, diethyl sulfide, dipropyl sulfide and propyl methyl sulfide, or also an organic disulfide of formula HO—$R_1$—S—S—$R_2$—OH, such as dithiodiethanol of formula HO—$C_2H_4$—S—S—$C_2H_4$—OH (often referred to as DEODS). The sulfur content is generally between 0.1% and 2% by weight of said element relative to the total weight of the catalyst.

Catalyst

The catalyst that can be obtained by means of the preparation process according to the invention comprises an active phase comprising nickel and copper, part of the nickel and copper of which is in the form of a nickel-copper alloy, advantageously corresponding to the formula $Ni_xCu_y$ with x between 0.1 and 0.9 and y between 0.1 and 0.9, and a support in the form of a refractory oxide chosen from silica, alumina and silica-alumina.

The copper content is between 0.5 and 15% by weight of copper element relative to the total weight of the catalyst, preferably between 0.5 and 12% by weight, preferably between 0.75 and 10% by weight, and even more preferentially between 1 and 9% by weight.

The total nickel content in the catalyst is between 1% and 35% by weight of nickel element relative to the total weight of the catalyst, preferably between 2% and 30% by weight, preferably between 3% and 27% by weight, and even more preferentially between 4% and 18% by weight.

The nickel content included in the copper-nickel alloy formed by the preparation process according to the invention is between 0.5% and 15% by weight of nickel element relative to the total weight of the catalyst, preferably between 1% and 12% by weight, and more preferentially between 1% and 10% by weight.

The porous support is chosen from the group consisting of silica, alumina and silica-alumina. Even more preferably, the support is alumina. The alumina may be present in all possible crystallographic forms: alpha, delta, theta, chi, rho, eta, kappa, gamma, etc., taken alone or as a mixture. Preferably, the support is chosen from alpha, delta, theta and gamma alumina.

The specific surface area of the porous support is generally greater than 5 $m^2/g$, preferably between 30 and 400 $m^2/g$, preferably between 50 and 350 $m^2/g$.

The total pore volume of the support is generally between 0.1 and 1.5 $cm^3/g$, preferably between 0.35 and 1.2 $cm^3/g$, and even more preferably between 0.4 and 1.0 $cm^3/g$, and even more preferably between 0.45 and 0.9 $cm^3/g$.

Said catalyst is generally presented in all the forms known to those skilled in the art, for example in the form of beads (generally having a diameter of between 1 and 8 mm), of extrudates, of blocks or of hollow cylinders. Preferably, it consists of extrudates with a diameter generally of between 0.5 and 10 mm, preferably between 0.8 and 3.2 mm and very preferably between 1.0 and 2.5 mm and with a mean length of between 0.5 and 20 mm. The term "mean diameter" of the extrudates is intended to mean the mean diameter of the circle circumscribed in the cross section of these extrudates. The catalyst can advantageously be presented in the form of cylindrical, multilobal, trilobal or quadrilobal extrudates. Preferably, its shape will be trilobal or quadrilobal. The shape of the lobes could be adjusted according to all the methods known from the prior art.

The specific surface area of the catalyst is generally greater than 5 $m^2/g$, preferably between 30 and 400 $m^2/g$, preferably between 50 and 350 $m^2/g$.

The total pore volume of the catalyst is generally between 0.1 and 1.5 $cm^3/g$, preferably between 0.35 and 1.2 $cm^3/g$, and even more preferably between 0.4 and 1.0 $cm^3/g$, and even more preferably between 0.45 and 0.9 $cm^3/g$.

The catalyst advantageously has a macroporous volume less than or equal to 0.6 ml/g, preferably less than or equal to 0.5 ml/g, more preferably less than or equal to 0.4 ml/g, and even more preferably less than or equal to 0.3 ml/g.

The mesoporous volume of the catalyst is generally at least 0.10 ml/g, preferably at least 0.20 ml/g, preferably between 0.25 ml/g and 0.80 ml/g, more preferably between 0.30 and 0.65 ml/g.

The median mesopore diameter can be between 3 and 25 nm, preferably between 6 and 20 nm and particularly preferably between 8 and 18 nm.

The catalyst advantageously exhibits a median macropore diameter of between 50 and 1500 nm, preferably between 80 and 1000 nm and more preferably still of between 250 and 800 nm.

Preferably, the catalyst exhibits a low microporosity; very preferably, it does not exhibit any microporosity.

Selective Hydrogenation Process

Another subject of the present invention is a process for the selective hydrogenation of polyunsaturated compounds containing at least 2 carbon atoms per molecule, such as diolefins and/or acetylenics and/or alkenylaromatics, also known as styrenics, present in a hydrocarbon feedstock having a final boiling point of less than or equal to 300° C., said process being carried out at a temperature of between 0 and 300° C., at a pressure of between 0.1 and 10 MPa, at a hydrogen/(polyunsaturated compounds to be hydrogenated) mole ratio of between 0.1 and 10 and at an hourly space velocity of between 0.1 and 200 $h^{-1}$ when the process is carried out in the liquid phase, or at a hydrogen/(polyunsaturated compounds to be hydrogenated) mole ratio of between 0.5 and 1000 and at an hourly space velocity of between 100 and 40 000 $h^{-1}$ when the process is carried out in the gas phase, in the presence of a catalyst obtained by the preparation process as described above in the description.

Monounsaturated organic compounds, such as, for example, ethylene and propylene, are at the root of the manufacture of polymers, of plastics and of other chemicals having added value. These compounds are obtained from natural gas, from naphtha or from gas oil which have been treated by steam cracking or catalytic cracking processes. These processes are carried out at high temperature and produce, in addition to the desired monounsaturated compounds, polyunsaturated organic compounds, such as acetylene, propadiene and methylacetylene (or propyne), 1,2-butadiene and 1,3-butadiene, vinylacetylene and ethylacetylene, and other polyunsaturated compounds, the boiling point of which corresponds to the C5+ fraction (hydrocarbon compounds having at least 5 carbon atoms), in particular diolefin or styrene or indene compounds. These polyunsaturated compounds are highly reactive and result in side reactions in the polymerization units. It is thus necessary to remove them before making economic use of these fractions.

Selective hydrogenation is the main treatment developed to specifically remove undesirable polyunsaturated compounds from these hydrocarbon feedstocks. It makes possible the conversion of polyunsaturated compounds to the corresponding alkenes or aromatics while avoiding their complete saturation and thus the formation of the corresponding alkanes or naphthenes. In the case of steam cracking gasolines used as feedstock, the selective hydrogenation also makes it possible to selectively hydrogenate the alkenylaromatics to give aromatics while avoiding the hydrogenation of the aromatic nuclei.

The hydrocarbon feedstock treated in the selective hydrogenation process has a final boiling point of less than or equal to 300° C. and contains at least 2 carbon atoms per molecule and comprises at least one polyunsaturated compound. The term "polyunsaturated compounds" is intended to mean compounds comprising at least one acetylenic function and/or at least one diene function and/or at least one alkenylaromatic function.

More particularly, the feedstock is selected from the group consisting of a steam cracking C2 fraction, a steam cracking C2-C3 fraction, a steam cracking C3 fraction, a steam cracking C4 fraction, a steam cracking C5 fraction and a steam cracking gasoline, also known as pyrolysis gasoline or C5+ fraction.

The steam cracking C2 fraction, advantageously used for the implementation of the selective hydrogenation process according to the invention, exhibits, for example, the following composition: between 40% and 95% by weight of ethylene relative to the total weight of said fraction, and of the order of 0.1% to 5% by weight of acetylene, the remainder being essentially ethane and methane. In some steam cracking C2 fractions, between 0.1% and 1% by weight of C3 compounds may also be present.

The steam cracking C3 fraction, advantageously used for the implementation of the selective hydrogenation process according to the invention, exhibits, for example, the following mean composition: of the order of 90% by weight of propylene relative to the total weight of said fraction, and of the order of 1% to 8% by weight of propadiene and of methylacetylene, the remainder being essentially propane. In some C3 fractions, between 0.1% and 2% by weight of C2 compounds and of C4 compounds may also be present.

A C2-C3 fraction can also advantageously be used for the implementation of the selective hydrogenation process according to the invention. It exhibits, for example, the following composition: of the order of 0.1% to 5% by weight of acetylene relative to the total weight of said fraction, of the order of 0.1% to 3% by weight of propadiene and of methylacetylene, of the order of 30% by weight of ethylene and of the order of 5% by weight of propylene, the remainder being essentially methane, ethane and propane. This feedstock may also contain between 0.1% and 2% by weight of C4 compounds.

The steam cracking C4 fraction, advantageously used for the implementation of the selective hydrogenation process according to the invention, exhibits, for example, the following mean composition by weight: 1% by weight of butane relative to the total weight of said fraction, 46.5% by weight of butene, 51% by weight of butadiene, 1.3% by weight of vinylacetylene and 0.2% by weight of butyne. In some C4 fractions, between 0.1% and 2% by weight of C3 compounds and of C5 compounds may also be present.

The steam cracking C5 fraction, advantageously used for the implementation of the selective hydrogenation process according to the invention, exhibits, for example, the following composition: 21% by weight of pentanes relative to the total weight of said fraction, 45% by weight of pentenes, 34% by weight of pentadienes.

The steam cracking gasoline or pyrolysis gasoline, advantageously used for the implementation of the selective hydrogenation process according to the invention, corresponds to a hydrocarbon fraction, the boiling point of which is generally between 0 and 300° C., preferably between 10 and 250° C. The polyunsaturated hydrocarbons to be hydrogenated present in said steam cracking gasoline are in particular diolefin compounds (butadiene, isoprene, cyclopentadiene, and the like), styrene compounds (styrene, α-methylstyrene, and the like) and indene compounds (indene, and the like). The steam cracking gasoline generally comprises the C5-C12 fraction with traces of C3, C4, C13, C14 and C15 (for example between 0.1% and 3% by weight for each of these fractions). For example, a feedstock formed of pyrolysis gasoline generally has a composition as follows: 5% to 30% by weight of saturated compounds (paraffins and naphthenes), 40% to 80% by weight of aromatic compounds, 5% to 20% by weight of mono-olefins, 5% to 40% by weight of diolefins and 1% to 20% by weight of alkenylaromatic compounds, the combined compounds forming 100%. It also contains from 0 to 1000 ppm by weight of sulfur, preferably from 0 to 500 ppm by weight of sulfur.

Preferably, the polyunsaturated hydrocarbon feedstock treated in accordance with the selective hydrogenation process according to the invention is a steam cracking C2 fraction or a steam cracking C2-C3 fraction or a steam cracking gasoline.

The selective hydrogenation process according to the invention is targeted at removing said polyunsaturated hydrocarbons present in said feedstock to be hydrogenated without hydrogenating the monounsaturated hydrocarbons. For example, when said feedstock is a C2 fraction, the selective hydrogenation process is targeted at selectively hydrogenating acetylene. When said feedstock is a C3 fraction, the selective hydrogenation process is targeted at selectively hydrogenating propadiene and methylacetylene. In the case of a C4 fraction, the aim is to remove butadiene, vinylacetylene (VAC) and butyne; in the case of a C5 fraction, the aim is to remove the pentadienes. When said feedstock is a steam cracking gasoline, the selective hydrogenation process is targeted at selectively hydrogenating said polyunsaturated hydrocarbons present in said feedstock to be treated so that the diolefin compounds are partially hydrogenated to give mono-olefins and so that the styrene and indene compounds are partially hydrogenated to give corresponding aromatic compounds while avoiding the hydrogenation of the aromatic nuclei.

The technological implementation of the selective hydrogenation process is, for example, carried out by injection, as ascending or descending stream, of the polyunsaturated hydrocarbon feedstock and of the hydrogen into at least one fixed bed reactor. Said reactor may be of isothermal type or of adiabatic type. An adiabatic reactor is preferred. The polyunsaturated hydrocarbon feedstock can advantageously be diluted by one or more reinjection(s) of the effluent, resulting from said reactor where the selective hydrogenation reaction takes place, at various points of the reactor, located between the inlet and the outlet of the reactor, in order to limit the temperature gradient in the reactor. The technological implementation of the selective hydrogenation process according to the invention can also advantageously be carried out by the implantation of at least said supported catalyst in a reactive distillation column or in reactors-exchangers or in a slurry-type reactor. The stream of hydrogen may be introduced at the same time as the feedstock to be hydrogenated and/or at one or more different points of the reactor.

The selective hydrogenation of the steam cracking C2, C2-C3, C3, C4, C5 and C5+ fractions can be carried out in the gas phase or in the liquid phase, preferably in the liquid phase for the C3, C4, C5 and C5+ fractions and in the gas phase for the C2 and C2-C3 fractions. A liquid-phase reaction makes it possible to lower the energy cost and to increase the cycle period of the catalyst.

Generally, the selective hydrogenation of a hydrocarbon feedstock containing polyunsaturated compounds containing at least 2 carbon atoms per molecule and having a final boiling point of less than or equal to 300° C. is carried out at a temperature of between 0 and 300° C., at a pressure of between 0.1 and 10 MPa, at a hydrogen/(polyunsaturated compounds to be hydrogenated) mole ratio of between 0.1 and 10 and at an hourly space velocity HSV (defined as the ratio of the flow rate by volume of feedstock to the volume of the catalyst) of between 0.1 and 200 $h^{-1}$ for a process carried out in the liquid phase, or at a hydrogen/(polyunsaturated compounds to be hydrogenated) mole ratio of between 0.5 and 1000 and at an hourly space velocity HSV of between 100 and 40 000 $h^{-1}$ for a process carried out in the gas phase.

In one embodiment according to the invention, when a selective hydrogenation process is carried out wherein the feedstock is a steam cracking gasoline comprising polyunsaturated compounds, the (hydrogen)/(polyunsaturated compounds to be hydrogenated) mole ratio is generally between 0.5 and 10, preferably between 0.7 and 5.0 and more preferably still between 1.0 and 2.0, the temperature is between 0 et 200° C., preferably between 20 and 200° C. and more preferably still between 30 and 180° C., the hourly space velocity (HSV) is generally between 0.5 and 100 $h^{-1}$, preferably between 1 and 50 $h^{-1}$, and the pressure is generally between 0.3 and 8.0 MPa, preferably between 1.0 and 7.0 MPa and more preferably still between 1.5 and 4.0 MPa.

More preferably, a selective hydrogenation process is carried out wherein the feedstock is a steam cracking gasoline comprising polyunsaturated compounds, the hydrogen/(polyunsaturated compounds to be hydrogenated) mole ratio is between 0.7 and 5.0, the temperature is between 20 and 200° C., the hourly space velocity (HSV) is generally between 1 and 50 $h^{-1}$ and the pressure is between 1.0 and 7.0 MPa.

More preferably still, a selective hydrogenation process is carried out wherein the feedstock is a steam cracking gasoline comprising polyunsaturated compounds, the hydrogen/(polyunsaturated compounds to be hydrogenated) mole ratio is between 1.0 and 2.0, the temperature is between 30 and 180° C., the hourly space velocity (HSV) is generally between 1 and 50 $h^{-1}$ and the pressure is between 1.5 and 4.0 MPa.

The hydrogen flow rate is adjusted in order to have available a sufficient amount thereof to theoretically hydrogenate all of the polyunsaturated compounds and to maintain an excess of hydrogen at the reactor outlet.

In another embodiment according to the invention, when a selective hydrogenation process is carried out wherein the feedstock is a steam cracking C2 fraction and/or a steam cracking C2-C3 fraction comprising polyunsaturated compounds, the (hydrogen)/(polyunsaturated compounds to be hydrogenated) mole ratio is generally between 0.5 and 1000, preferably between 0.7 and 800, the temperature is between 0 et 300° C., preferably between 15 and 280° C., the hourly space velocity (HSV) is generally between 100 and 40 000 $h^{-1}$, preferably between 500 and 30 000 $h^{-1}$, and the pressure is generally between 0.1 and 6.0 MPa, preferably between 0.2 and 5.0 MPa.

The invention will now be illustrated by the following examples which are in no way limiting.

EXAMPLES

For all the catalysts mentioned in the examples mentioned below, the support is an alumina A having a specific surface area of 80 $m^2/g$, a pore volume of 0.7 ml/g ($cm^3/g$) and a median mesopore diameter of 12 nm.

Example 1: Preparation of an Aqueous Solution of Ni Precursors

The aqueous solution of Ni precursors (solution S) used for the preparation of the catalysts A to E is prepared by dissolving 43.5 g of nickel nitrate ($NiNO_3$ (supplier Strem Chemicals®)) in a volume of 13 ml of distilled water. The solution S, the Ni concentration of which is 350 g of Ni per liter of solution, is obtained.

Example 2: Catalyst A—15% by Weight of Ni (Comparative)

The solution S prepared in example 1 is impregnated under dry conditions on 10 g of alumina A. The solid thus obtained is subsequently dried in an oven overnight at 120° C. and then calcined under a stream of air of 1 l/h/g of catalyst at 450° C. for 2 hours. The calcined catalyst thus prepared contains 15% by weight of the nickel element relative to the total weight of the alumina-supported catalyst.

The catalyst precursor is then reduced under the conditions as described in example 8 below.

Example 3: Catalyst B—15% by Weight of Ni+ of Cu in Co-Impregnation with a Ni/Cu Ratio=3 (Comparative)

A copper nitrate solution is prepared so as to finally obtain a Ni/Cu ratio=3 on the final catalyst and dry-co-impregnated, with the solution S prepared in example 1, on 10 g of alumina A. The solid thus obtained is then dried in an oven overnight at 120° C. The solid thus obtained is then dried in an oven overnight at 120° C., then calcined under a stream of air of 1 l/h/g of catalyst at 450° C. for 2 hours.

The catalyst precursor is then reduced under the conditions as described in example 8 below.

Example 4: Catalyst C—Impregnation of Ni+Cu (5% by Weight Ni and Ni/Cu Mole Ratio=3) Followed by Impregnation of 15% by Weight of Ni (According to the Invention)

A copper nitrate solution is prepared so as to finally obtain a Ni/Cu ratio=3 on the intermediate catalyst and dry-co-impregnated with the solution S prepared in example 1, on 10 g of alumina A. The Ni content is 5% by weight relative to the weight of the final catalyst. The solid thus obtained is subsequently dried in an oven overnight at 120° C., and then calcined under a stream of air of 1 l/h/g of catalyst at 450° C. for 2 hours. This is then reduced under a hydrogen pressure at 190° C. for 4 h then returned to air. The catalyst precursor C1 is obtained. The solution S is then dry-impregnated on the catalyst precursor C1 so as to obtain 15% by weight of Ni alone, relative to the total weight of the final catalyst (which does not contribute to the alloy). The solid thus obtained is subsequently dried in an oven overnight at 120° C., and then calcined under a stream of air of 1 l/h/g of catalyst at 450° C. for 2 hours. The catalyst precursor is then reduced under the conditions as described in example 8 below.

Example 5: Catalyst D—Ni+Cu Impregnation (2% by Weight of Ni and Ni/Cu Mole Ratio=3) Followed by Impregnation of 15% by Weight of Ni (According to the Invention)

A copper nitrate solution is prepared so as to finally obtain a Ni/Cu ratio=3 on the intermediate catalyst and dry-co-impregnated with the solution S prepared in example 1, on 10 g of alumina A. The Ni content is 2% by weight relative to the weight of the final catalyst. The solid thus obtained is subsequently dried in an oven overnight at 120° C., and then calcined under a stream of air of 1 l/h/g of catalyst at 450° C. for 2 hours. This is then reduced under a hydrogen stream at 190° C. for 4 h then returned to air. The catalyst precursor D1 is obtained.

The solution S is then dry-impregnated on the catalyst precursor D1 so as to obtain 15% by weight of Ni alone, relative to the total weight of the final catalyst (which does not contribute to the alloy). The solid thus obtained is subsequently dried in an oven overnight at 120° C., and then calcined under a stream of air of 1 l/h/g of catalyst at 450° C. for 2 hours. The catalyst precursor is then reduced under the conditions as described in example 8 below.

Example 6: Catalyst E—Ni+Cu Impregnation (5% by Weight of Ni and Ni/Cu Mole Ratio=2) Followed by Impregnation of 15% by Weight of Ni (According to the Invention)

A copper nitrate solution is prepared so as to finally obtain a Ni/Cu ratio=2 on the intermediate catalyst and dry-co-impregnated with the solution S prepared in example 1, on 10 g of alumina A. The Ni content is 5% by weight relative to the weight of the final catalyst. The solid thus obtained is subsequently dried in an oven overnight at 120° C., and then calcined under a stream of air of 1 l/h/g of catalyst at 450° C. for 2 hours. This is then reduced under a hydrogen stream at 190° C. for 4 h then returned to air. The catalyst precursor E1 is obtained. The solution S is then dry-impregnated on the catalyst precursor E1 so as to obtain 15% by weight of Ni alone, relative to the total weight of the final catalyst (which does not contribute to the alloy). The solid thus obtained is subsequently dried in an oven overnight at 120° C., and then calcined under a stream of air of 1 l/h/g of catalyst at 450° C. for 2 hours.

The catalyst precursor is then reduced under the conditions as described in example 8 below.

Example 7: Characterization

All the catalysts contain the contents targeted during impregnation, that is to say 15% of nickel element (characterized by X-ray Fluorescence) relative to the total weight of the catalyst, and the % of copper added (characterized by X-ray Fluorescence).

The amount of alloy obtained after the calcination then reduction step was determined by X-ray diffraction (XRD) analysis on samples of the catalyst in powder form.

The amount of nickel in metallic form obtained after the reduction step was determined by X-ray diffraction (XRD) analysis on samples of catalyst in powder form. Between the reduction step and throughout the duration of the characterization by XRD, the catalysts are never returned to the open air. The diffraction patterns are obtained by radio crystallographic analysis by means of a diffractometer using the conventional powder method with K$\alpha$1 radiation of copper ($\lambda$=1.5406 Å).

The degree of reduction was calculated by calculating the area of the line of $Ni^0$ located around 52° 2θ, on all of the diffractograms of each sample of catalyst analyzed, then by subtracting the signal present as soon as ambient temperature is reached under the line at 52°, which is due to alumina.

Table 1 below collates the degrees of reduction or else the content of nickel metal $Ni^0$ (expressed as % by weight relative to the total weight of Ni) for all the catalysts A to E characterized by XRD after a reduction step at 190° C. for 90 minutes under a hydrogen stream.

These values were also compared with the degree of reduction obtained for catalyst A (Ni alone) after a conventional reduction step (that is to say at a temperature of 400° C. for 15 hours under a hydrogen stream).

Alumina in delta and theta form and large CuO and NiO lines are detected at ambient temperature on all the copper- and nickel-containing catalysts, after calcination. A line corresponding to the alloy in $Ni_{0.76}Cu_{0.24}$ form is moreover detected after reduction.

In order to evaluate the degree of reducibility and therefore the formation of $Ni^0$, the area of the line of $Ni^0$ located around 52° 2θ is measured, on all the diffractograms, by subtracting the signal present from ambient temperature under the line at 52° and which is due to the alumina. It is thus possible to determine the relative percentage of $Ni^0$ crystallized after reduction.

Table 1 below summarizes the degrees of reducibility or the $Ni^o$ content for all the catalysts characterized by XRD after reduction at 190° C. for 90 minutes under a hydrogen stream. These values were also compared with the degree of reduction obtained for catalyst A (Ni alone) after a conventional reduction step (that is to say at a temperature of 400° C. for 15 hours under a hydrogen stream).

TABLE 1

| Catalyst | Final reduction | Ni content for the 1$^{st}$ imp. (wt %) | Ni content for 2$^{nd}$ imp. (wt %) | Ni/Cu mole ratio for the 1st imp. | Percentage of Ni$^o$ alone (XRD) after reduction (%) |
|---|---|---|---|---|---|
| A (comparative) | 400° C., 15 h | — | 15 | — | 80 |
| A (comparative) | 190° C., 90 min | — | 15 | — | 0* |
| B (comparative) | 190° C., 90 min | 15 | — | 3 | 0** |

TABLE 1-continued

| Catalyst | Final reduction | Ni content for the 1st imp. (wt %) | Ni content for 2nd imp. (wt %) | Ni/Cu mole ratio for the 1st imp. | Percentage of Ni° alone (XRD) after reduction (%) |
|---|---|---|---|---|---|
| C (invention) | 190° C., 90 min | 5 | 15 | 3 | 100 |
| D (invention) | 190° C., 90 min | 2 | 15 | 3 | 90 |
| E (invention) | 190° C., 90 min | 5 | 15 | 2 | 70 |

*Nickel in NiO form
**Nickel in alloy form

For catalyst A (15% Ni alone/alumina), the degree of nickel reducibility is 0% after exactly the same reduction treatment under hydrogen as for the catalysts B to E.

The pre-impregnation of nickel (5% by weight of Ni) and of copper with a Ni/Cu ratio of 2 makes it possible to obtain reduced Ni° of the order of 70% in the end on the catalyst. The pre-impregnation of less NiCu alloy with a content of nickel making up the alloy of 2% by weight and of copper with a Ni/Cu ratio of 3 makes it possible to obtain reduced Ni° of the order of 90% in the end on the catalyst. The pre-impregnation of nickel (5% by weight of Ni) and of copper with a Ni/Cu ratio of 3 makes it possible to obtain 100% of reduced Ni° from 170° C. in the end on the catalyst.

Example 8: Catalytic Tests: Performance Levels in Selective Hydrogenation of a Mixture Containing Styrene and Isoprene ($A_{HYD1}$)

Catalysts A to E described in the examples above are tested with regard to the reaction for the selective hydrogenation of a mixture containing styrene and isoprene.

The composition of the feedstock to be selectively hydrogenated is as follows: 8% by weight of styrene (supplied by Sigma Aldrich®, purity 99%), 8% by weight of isoprene (supplied by Sigma Aldrich®, purity 99%) and 84% by weight of n-heptane (solvent) (supplied by VWR®, purity >99% Chromanorm HPLC). This composition corresponds to the initial composition of the reaction mixture. This mixture of model molecules is representative of a pyrolysis gasoline.

The selective hydrogenation reaction is carried out in a 500 ml stainless steel autoclave which is provided with a magnetically-driven mechanical stirrer and which is able to operate under a maximum pressure of 100 bar (10 MPa) and temperatures of between 5° C. and 200° C.

214 ml of n-heptane (supplied by VWR®, purity>99% Chromanorm HPLC) and an amount of 3 ml of catalyst are added to an autoclave. The autoclave is closed and purged. The autoclave is then pressurized under 35 bar (3.5 MPa) of hydrogen. The catalyst is first reduced in situ, at 190° C. for 90 minutes under a hydrogen pressure (temperature rise gradient of 1° C./min) for catalysts A to E (which corresponds here to step h) of the preparation process according to the invention according to one embodiment). The autoclave is then brought to the test temperature equal to 30° C. At time t=0, approximately 30 g of a mixture containing styrene, isoprene, n-heptane, pentanethiol and thiophene are introduced into the autoclave. The reaction mixture then has the composition described above and stirring is started at 1600 rev/min. The pressure is kept constant at 35 bar (3.5 MPa) in the autoclave using a storage cylinder located upstream of the reactor.

Another test was carried out for catalyst A, but with a catalyst reduction temperature of 400° C. for 15 hours.

The progress of the reaction is monitored by taking samples from the reaction medium at regular time intervals: the styrene is hydrogenated to give ethylbenzene, without hydrogenation of the aromatic ring, and the isoprene is hydrogenated to give methylbutenes. If the reaction is prolonged for longer than necessary, the methylbutenes are in their turn hydrogenated to give isopentane. The hydrogen consumption is also monitored over time by the decrease in pressure in a storage cylinder located upstream of the reactor. The catalytic activity is expressed in moles of $H_2$ consumed per minute and per gram of Ni.

The catalytic activities measured for catalysts A to E are reported in table 2 below. They are related to the catalytic activity ($A_{HYD1}$) measured for catalyst A prepared under conventional reduction conditions (at a temperature of 400° C. for 15 hours under a hydrogen stream).

TABLE 2

| Catalyst | Final reduction | Ni content for the 1st imp. (wt %) | Ni content for 2nd imp. (%) | Ni/Cu ratio for the 1st imp. | Percentage of Ni° (XRD) after reduction (%) | $A_{HYD1}$ (%) |
|---|---|---|---|---|---|---|
| A (comparative) | 400° C., 15 h | — | 15 | — | 80 | 100 |
| A (comparative) | 190° C., 90 min | — | 15 | — | 0 | 0 |
| B (comparative) | 190° C., 90 min | 15 | — | 3 | 0 | 30 |
| C (invention) | 190° C., 90 min | 5 | 15 | 3 | 100 | 180 |
| D (invention) | 190° C., 90 min | 2 | 15 | 3 | 90 | 140 |
| E (invention) | 190° C., 90 min | 5 | 15 | 2 | 70 | 100 |

This clearly shows the improved performance of catalysts C, D and E according to the invention, compared with the catalyst Ni alone on alumina (catalyst A) reduced at 190° C. for 90 min, which is completely inactive. Moreover, it should be noted that the NiCu alloy alone (catalyst B) has an activity which is very much behind the reference (of the order of 30%).

The invention claimed is:

1. A process for preparing a catalyst for the selective hydrogenation of polyunsaturated hydrocarbon fractions comprising nickel, in a proportion of 1% to 35% by weight of nickel element relative to the total weight of the catalyst, and copper, in a proportion of 0.5% to 15% by weight of copper element relative to the total weight of the catalyst, and a support comprising at least one refractory oxide chosen from silica, alumina and silica-alumina, said process comprising:
   a) a step of bringing the support into contact with at least one solution containing at least one copper precursor and one nickel precursor at a desired nickel concentration is carried out in order to obtain, on the final catalyst, a content of between 0.5% and 15% by weight of nickel element relative to the total weight of the final catalyst;
   b) at least one step of drying the catalyst precursor resulting from step a) is carried out at a temperature of less than 250° C.;
   c) optionally, a heat treatment of the catalyst precursor obtained at the end of step b) is carried out at a temperature of between 250 and 1000° C., in the presence or absence of water;
   d) the catalyst precursor resulting from step b), or optionally from step c), is reduced by bringing said catalyst precursor into contact with a reducing gas at a temperature of between 150 and 250° C.;
   e) a step of bringing the catalyst precursor obtained at the end of step d) into contact with a solution comprising at least one nickel precursor is carried out;
   f) at least one step of drying the catalyst precursor resulting from step e) is carried out at a temperature of less than 250° C.;
   g) optionally, a heat treatment of the catalyst precursor obtained at the end of step f) is carried out at a temperature of between 250 and 1000° C., in the presence or absence of water;
   h) the catalyst precursor resulting from step f), or optionally from step g), is reduced by bringing said catalyst precursor into contact with a reducing gas at a temperature of between 150 and 250° C.,
   wherein steps d) and/or step h) is (are) carried out for between 10 minutes and 110 minutes.

2. The process as claimed in claim 1, wherein, in step a), the mole ratio between nickel and copper is between 0.5 and 5.

3. The process as claimed in claim 2, wherein, in step a), the mole ratio between nickel and copper is between 0.7 and 4.5.

4. The process as claimed in claim 2, wherein, in step a), the mole ratio between nickel and copper is between 0.9 and 4.

5. The process as claimed in claim 1, wherein step d) and/or step h) is (are) carried out at a temperature of between 160 and 230° C.

6. The process as claimed in claim 1, wherein step d) and/or step h) is (are) carried out at a temperature of between 170 and 220° C.

7. The process as claimed in claim 1, further comprising a step of passivation of the catalyst precursor with a sulfur-containing compound after reduction step d) but before step e), and/or after reduction step h).

8. The process as claimed in claim 7, wherein the passivation step(s) is (are) carried out at a temperature of between 20 and 350° C. for 10 to 240 minutes.

9. The process as claimed in claim 7, wherein said sulfur-containing compound is thiophene, thiophane, dimethyl sulfide, diethyl sulfide, dipropyl sulfide, propylmethyl sulfide, or dithiodiethanol.

10. The process as claimed in claim 1, wherein the copper precursor is copper acetate, copper acetylacetonate, copper nitrate, copper sulfate, copper chloride, copper bromide, copper iodide, or copper fluoride.

11. The process as claimed in claim 10, wherein the copper precursor is copper nitrate.

12. The process as claimed in claim 1, wherein the reducing gas of step d) and/or step h) is dihydrogen.

13. The process as claimed in claim 12, wherein the dihydrogen flow rate, expressed in l/hour/gram of catalyst precursor, is between 0.01 and 100 l/hour/gram of catalyst precursor.

14. The process as claimed in claim 1, wherein the nickel precursor supplied during step a) and/or step e) is nickel nitrate, nickel carbonate, or nickel hydroxide.

15. The process as claimed in claim 1, wherein the nickel content in the catalyst is between 2% and 30% by weight of nickel element relative to the total weight of the catalyst.

16. The process as claimed in claim 1, wherein the copper content in the catalyst is between 0.5 and 12% by weight of copper element relative to the total weight of the catalyst.

17. The process as claimed in claim 1, wherein the specific surface area of the support is between 30 and 400 $m^2/g$.

18. The process as claimed in claim 1, wherein the total pore volume of the support is between 0.1 and 1.5 $cm^3/g$.

19. A process for the selective hydrogenation of polyunsaturated compounds containing at least 2 carbon atoms per molecule, present in a hydrocarbon feedstock having a final boiling point of less than or equal to 300° C., said process comprising:
   conducting the selective hydrogenation at a temperature of between 0 and 300° C., at a pressure of between 0.1 and 10 MPa, at a hydrogen/(polyunsaturated compounds to be hydrogenated) mole ratio of between 0.1 and 10 and at an hourly space velocity of between 0.1 and 200 lf when the process is carried out in the liquid phase, in the presence of a catalyst prepared by the process according to claim 1, or
   conducting the selective hydrogenation at a hydrogen/(polyunsaturated compounds to be hydrogenated) mole ratio of between 0.5 and 1000 and at an hourly space velocity of between 100 and 40 000 $h^{-1}$ when the process is carried out in the gas phase, in the presence of a catalyst prepared by the process according to claim 1.

* * * * *